(12) United States Patent
Kreindel

(10) Patent No.: US 11,464,970 B2
(45) Date of Patent: Oct. 11, 2022

(54) METHOD FOR ENHANCED ELECTRO-MUSCLE STIMULATION

(71) Applicant: Inmode Ltd., Yokneam (IL)

(72) Inventor: Michael Kreindel, Richmond Hill (CA)

(73) Assignee: Inmode Ltd., Yokneam (IL)

(*) Notice: Subject to any disclaimer, the term of this patent is extended or adjusted under 35 U.S.C. 154(b) by 0 days.

(21) Appl. No.: 16/819,110

(22) Filed: Mar. 15, 2020

(65) Prior Publication Data
US 2021/0283395 A1    Sep. 16, 2021

(51) Int. Cl.
*A61N 1/04* (2006.01)
*A61N 1/36* (2006.01)
*A61N 5/06* (2006.01)

(52) U.S. Cl.
CPC ....... *A61N 1/36003* (2013.01); *A61N 1/0452* (2013.01); *A61N 5/0616* (2013.01); *A61N 5/0622* (2013.01); *A61N 5/0625* (2013.01)

(58) Field of Classification Search
CPC .............. A61N 1/36006; A61N 5/0616; A61N 5/0622; A61N 5/0625
See application file for complete search history.

(56) References Cited

U.S. PATENT DOCUMENTS

| | | |
|---|---|---|
| 6,021,348 A | 2/2000 | James |
| 7,238,183 B2 | 7/2007 | Kreindel |
| 8,588,901 B2 | 11/2013 | Fahey |
| 9,149,386 B2 | 10/2015 | Fahey et al. |
| 9,532,899 B2 | 1/2017 | Fahey et al. |
| 9,937,358 B2 | 4/2018 | Schwarz et al. |
| 10,124,187 B2 | 11/2018 | Schwarz et al. |
| 10,207,107 B2 | 2/2019 | Dai et al. |
| 10,478,622 B2 | 11/2019 | Fahey |
| 10,569,094 B2 | 2/2020 | Schwarz et al. |
| 10,821,295 B1 * | 11/2020 | Schwarz ................ A61B 18/02 |

* cited by examiner

*Primary Examiner* — Lynsey C Eiseman
*Assistant Examiner* — Jessica L Mullins
(74) *Attorney, Agent, or Firm* — Dekel Patent Ltd.; David Klein

(57) ABSTRACT

The invention relates to an enhanced method of electrical muscle stimulation.

13 Claims, 2 Drawing Sheets

METHOD FOR ENHANCED ELECTRO-MUSCLE STIMULATION

FIELD OF THE INVENTION

The invention relates to preheating of skin and subcutaneous tissue for better delivery of electrical energy to the deeper muscles to provide enhanced electrical muscle stimulation (EMS).

BACKGROUND OF THE INVENTION

The invention of electrical muscle stimulation is credited to Luigi Galvani. Half a century ago, EMS started to be used in sports medicine, mostly for muscle rehabilitation. Recently, EMS has been employed in aesthetic medicine for muscle strengthening and fat reduction. Muscle stimulation is induced by an electrical current applied over the tissue in the vicinity of stimulated muscle.

Alternatively, radiative electromagnetic energy can be used as a method to stimulate muscle contraction (U.S. patent Ser. No. 10/569,094, 10/124,187, U.S. Pat. No. 9,937,358).

Electrical tissue parameters depend on tissue temperature. The tissue heating reduces tissue viscosity and increase tissue conductivity by approximately 2% per one degree centigrade (FA Duck, Physical properties of tissue, Academic Press, 1990, p. 173). This effect is used for RF and EMS devices but it is not dramatic.

U.S. patent Ser. No. 10/478,622 describes a device with multiplexing of two electrical signals and describes cooling and heating of tissue to effect viscosity and impedance of the tissue in the range of temperatures up to 40° C.

U.S. Pat. Nos. 9,532,899, 9,149,386 and 8,588,901 describe devices for stimulation of tissue where tissue is pre-cooled to reduce electrical current over the skin surface.

Higher frequency electrical pulses are used for transcutaneous electric nerve stimulation (TENS) mostly for pain reduction and muscle relaxation.

While both heating and electrical pulses work in favor of pain reduction and muscle relaxation there are devices that combine these two treatment modalities, such as U.S. patent Ser. No. 10/207,107 and U.S. Pat. No. 6,021,348.

Selective preheating of a specific part of tissue using optical energy prior to using RF energy is described in U.S. Pat. No. 7,238,183. This method supposedly improves treatment selectivity for such skin treatments as hair removal, vascular and pigmented lesion removal.

However, delivering electrical current to muscles through the thick layer of subcutaneous fat requires application of higher voltages, which in the prior art causes discomfort as a result of nerve stimulation in skin and fat.

SUMMARY OF THE INVENTION

The present invention provides a method for EMS including irritation of the tissue to increase blood circulation and to reduce skin and fat impedance prior to application of EMS pulses.

Increasing blood circulation is a reaction that typically appears as skin redness. It is the response of the tissue to heating, massaging, negative pressure (suction) or any other type of irritation.

To affect tissue properties significantly, the tissue can be heated deeply and uniformly up to sub-necrotic temperatures. Typical tissue temperatures which improve blood circulation are in the range of 40 to 50° C.

The tissue can be heated using optical energy such as a laser, intense pulsed light (IPL), infrared lamp or high power LED. However, the disadvantage of this method is sensitivity to skin pigmentation and limited penetration depth of light.

Alternatively, tissue can be heated by heat conduction from applied warm elements which can be preheated or actively warmed during the treatment. Microwave energy is another alternative for tissue heating.

The more preferable method is to use RF energy. Monopolar or bi-polar RF technology can be used, but for treatment of large areas, the bi-polar system is preferable to prevent thermal effects near the return electrode. Tissue impedance and RF parameters can be monitored by the system for each element and RF energy can be adjusted according to measurements. If measured impedance is out of the accepted range, the RF energy can be stopped. With large area electrodes and good coupling, the RF energy can be delivered directly from the electrodes to the skin. Alternatively, gel or conductive pads can be used for coupling between electrodes and the treated tissue.

Negative pressure can be used for coupling skin to the RF electrode located in the cavity connected to a vacuum pump.

A temperature sensor can be embedded into the electrodes or applicator to control the heating process. RF energy can be adjusted according to feedback from the one or more temperature sensors. Temperature sensors can be thermistors, thermocouples, optical sensors or other.

The typical average RF energy density may be, without limitation, in the range of 0.1 W/cm$^2$ to 10 W/cm$^2$. RF energy can be reduced when the target temperature is approached. RF energy can be switched on and off to maintain target temperature for the predetermined treatment time. The treatment time may be varied, without limitation, from 1 min and up to 120 min Heat exposure time may be, without limitation, in the range of 5 min to 60 min to reach deep and uniform heating.

RF frequency may be, without limitation, in the range of 100 kHz up to 40 MHz. The preferable range may be, without limitation, 400 kHz to 6 MHz.

After tissue heating, the EMS pulses are applied to the preheated area. The EMS pulses may be applied during two hours following the tissue heating before conductivity of the tissue is restored to the normal level. Alternatively, heat and EMS pulses can be applied simultaneously.

The same electrodes can be used for delivering RF energy and EMS pulses.

EMS can be induced by applying electrical energy using one or more electrodes applied to the skin surface. Alternatively, muscle contraction can be stimulated by electrical or magnetic field irradiated to the tissue.

Typical pulse widths of muscle contraction may be, without limitation, from 10 microseconds to 1 millisecond, delivered with a frequency of 0.5 Hz to 300 KHz. Pulses may be delivered, without limitation, during a time period of 0.2-10 sec followed by a resting period. Amplitude of the electrical energy may be adjusted to cause muscle contraction but without significant discomfort.

The current method can be used to improve muscle strength, to reduce cellulite and to increase muscle volume.

DETAILED DESCRIPTION

In addition to changing tissue physical parameters, heating above 40° C. increases blood circulation in the dermis and subcutaneous fat. Blood electrical conductivity is significantly higher than conductivity of skin and fat. The higher the blood content the higher the tissue conductivity.

Figure 2:
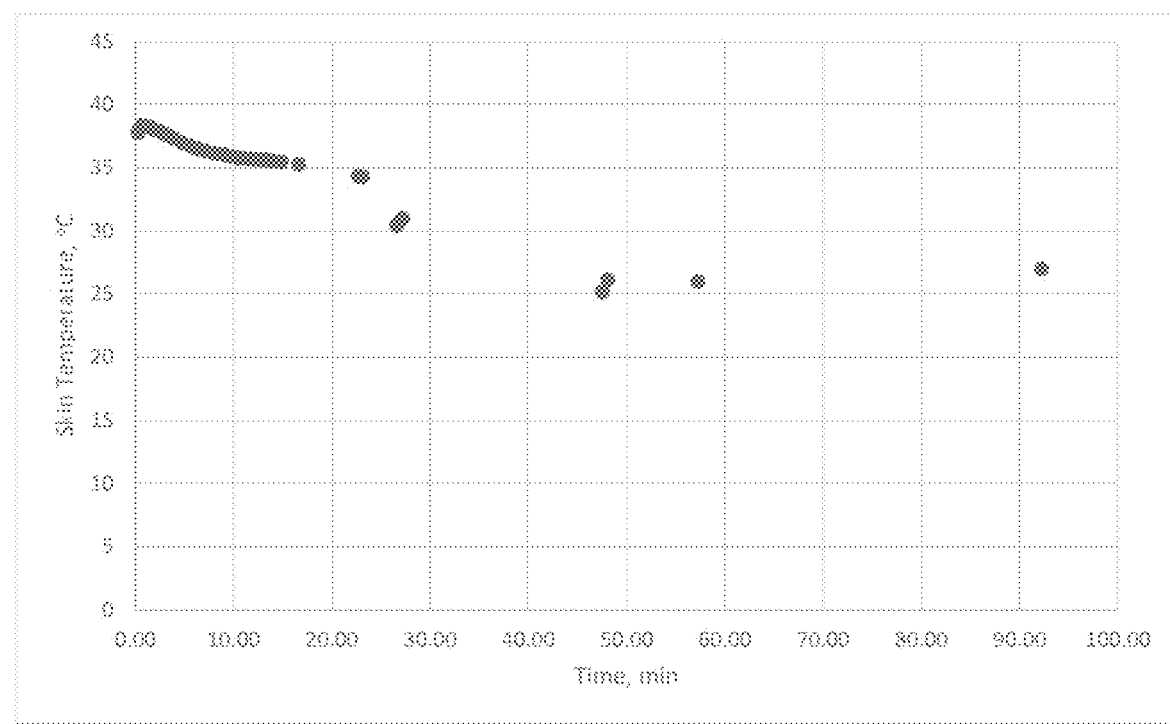
FIG. 2 is measured skin temperature in the abdominal area following preheating up to 41° C. for 30 min.

To prove the concept the following experiment was conducted. In-vivo abdominal tissue impedance was measured prior to heating. The skin was afterwards heated using bi-polar 1 MHz RF energy up to 43° C. and maintained for 30 min. Then EMS electrodes were applied to the same area after heat application and EMS voltage and current were measured over 90 min to monitor tissue impedance. A temperature sensor was embedded into the EMS electrodes and skin temperature was monitored. Because the initial electrode temperature was lower than the skin temperature, the initial temperature behavior included electrode temperature balancing with the treated tissue in the initial part of the graph in FIG. 2. Thus, as seen at the first minute or so of FIG. 2, the sensor was initially heated by the skin whereas the skin was cooled by the electrodes having a lower temperature than the skin surface.

Figure 1:
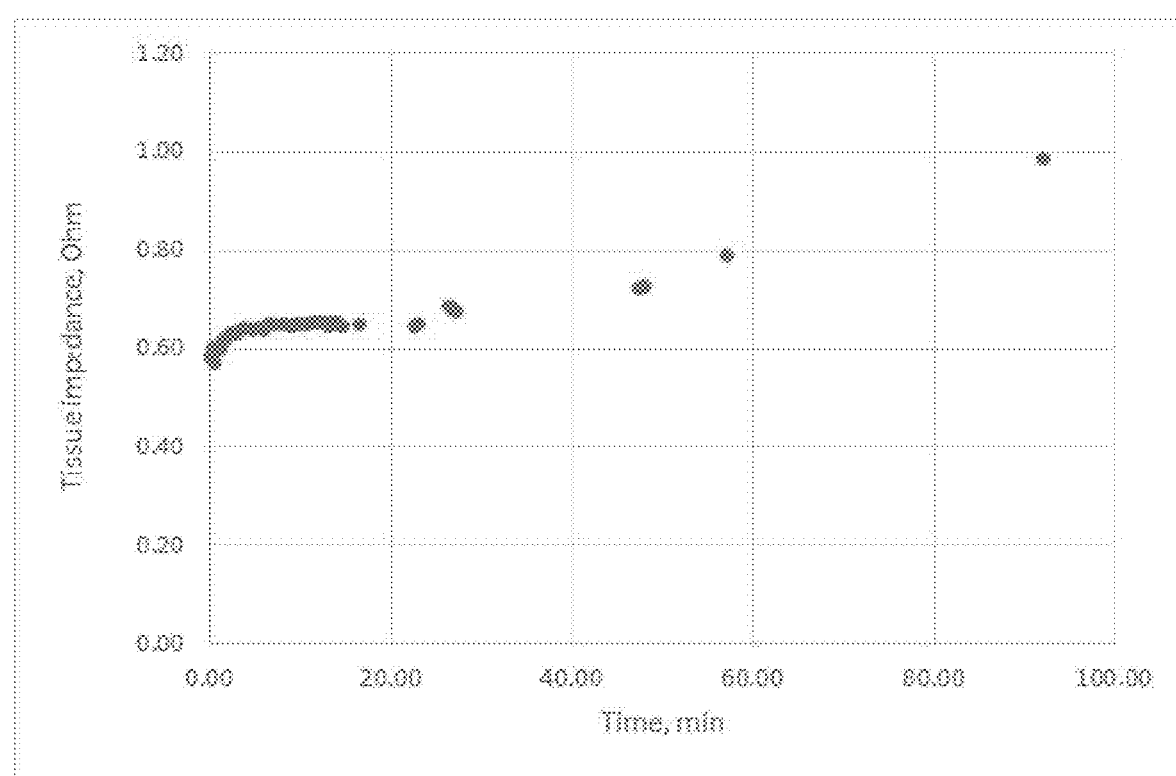
FIG. 1 is measured tissue impedance in the abdominal area following preheating up to 41° C. for 30 min.

Normalized tissue impedance as a function of time following tissue heating is shown in FIG. 1. Temperature behavior was measured with a temperature sensor embedded into the EMS electrode, and is shown as a function of time in FIG. 2. One can see in FIG. 1 that the tissue impedance rose sharply by 10% during a few seconds when the cold EMS unit was attached to the skin and the skin temperature dropped. Afterwards the tissue impedance stays stable over the next 25 minutes despite a temperature decrease by 5° C. After 25 min the tissue impedance starts to increase and continues to rise even after temperature of the skin reached a minimum and stabilized at around 26-28° C. (room temperature was 22° C.). The experiment shows that tissue conductivity does not correlate with temperature directly but rather correlates with skin erythema which was strong over the first 25 min following the treatment and then slowly decreased over the next 60 min. It is important to note that the feeling of EMS pulses in the tissue with erythema was much stronger than in areas which were not pre-heated.

The method of muscle stimulation without limitation includes the following steps:

1. Preheating of skin and subcutaneous tissue using RF energy
2. Monitoring tissue temperature
3. Maintaining tissue temperature in a range of 40° C. to 50° C. for about 5-30 min.
4. Applying EMS pulses to cause muscle contraction to the preheated tissue The preferred parameters for the RF energy used for tissue heating are, without limitation:

1. One or more RF electrodes applied to the skin surface
2. RF peak voltage applied to the tissue in the range of 10V up to 1000V
3. RF frequency in the range of 100 kHz up to 40 MHz
4. Temperature sensor embedded into applicator for tissue temperature monitoring.
5. RF energy is controlled according to feedback from temperature sensor and impedance measurements.

Preferred parameters for EMS without limitation:

1. EMS application during one hour following tissue heating
2. EMS voltage in the range of 5V to 100V
3. EMS pulse width in the range of 10-1000 microseconds
4. Wave form is biphasic pulse
5. Frequency of 1 Hz to 200 KHz

The invention claimed is:

1. A method for muscle stimulation comprising:
   irritating skin and subcutaneous fat to increase blood circulation in a treatment area;
   applying electromagnetic pulses to stimulate muscle in said treatment area; and
   maintaining muscle stimulation during a period of time while blood circulation is being increased, and further comprising applying said electromagnetic pulses for a period of time following increase of said blood circulation before conductivity of tissue in said treatment area is restored to normal conductivity level.

2. The method according to claim 1, wherein irritating skin and subcutaneous fat is done by applying RF energy to the skin and the subcutaneous fat.

3. The method according to claim 1, wherein irritating skin and subcutaneous fat is done by applying optical energy to the skin and the subcutaneous fat.

4. The method according to claim 1, wherein irritating skin and subcutaneous fat is done by applying negative pressure to the skin and the subcutaneous fat.

5. The method according to claim 1, wherein increasing blood circulation in the treatment area is done by heating the treatment area.

6. The method according to claim 1, wherein tissue irritation is done simultaneously with muscle stimulation.

7. The method according to claim 1, wherein tissue irritation is done prior to muscle stimulation.

8. The method according to claim 1, wherein maintaining muscle stimulation is done for up to 90 minutes following tissue irritation.

9. The method according to claim 1, wherein muscle stimulation is done by electrical current delivered using one or more electrodes.

10. The method according to claim 1, wherein muscle stimulation is done by using pulses delivered to the treatment area as a pulsed electromagnetic field.

11. The method according to claim 1, wherein tissue irritation is done by heating tissue to a sub-necrotic temperature.

12. The method according to claim 11, wherein the sub-necrotic temperature is 40° C. to 50° C.

13. The method according to claim 1, comprising heating skin to penetrate down to muscle tissue.

\* \* \* \* \*